United States Patent [19]
Takasugi et al.

[11] Patent Number: 5,599,798
[45] Date of Patent: Feb. 4, 1997

[54] CYCLIC AMP DERIVATIVE-CONTAINING OINTMENT

[75] Inventors: Norio Takasugi; Eiichi Mafune; Masayuki Takahashi, all of Tokyo, Japan

[73] Assignee: Daiichi Pharmaceutical Co., Ltd., Tokyo, Japan

[21] Appl. No.: 332,047

[22] Filed: Nov. 1, 1994

Related U.S. Application Data

[63] Continuation of Ser. No. 9,110, Jan. 26, 1993, abandoned.

[30] Foreign Application Priority Data

Jan. 27, 1992 [JP] Japan ................................. 4-011545

[51] Int. Cl.$^6$ ........................................................ A61K 31/70
[52] U.S. Cl. ........................ 514/47; 514/45; 514/46; 514/951; 514/969; 536/26.1; 536/26.12; 536/26.13
[58] Field of Search .................... 536/26.1, 26.12, 536/26.13; 514/47, 48, 46, 969, 951, 45

[56] References Cited

U.S. PATENT DOCUMENTS

| | | | |
|---|---|---|---|
| 4,369,181 | 1/1983 | Miller et al. | 424/180 |
| 4,873,227 | 10/1989 | Ikada et al. | 514/47 |
| 4,952,560 | 8/1990 | Kigasawa et al. | 514/2 |
| 5,096,891 | 3/1992 | Hirota et al. | 514/47 |

FOREIGN PATENT DOCUMENTS 1357731  6/1974  United Kingdom.

*Primary Examiner*—James O. Wilson
*Attorney, Agent, or Firm*—Sughrue, Mion, Zinn, Macpeak & Seas

[57] ABSTRACT

An ointment comprising an adenosine 3',5'-cyclic phosphate derivative, a base having water-absorbing and drying properties and, incorporated in the base, is one or more salts each having pH in an aqueous solution of from 3 to 7. The ointment maintains the active ingredient in a stable state over an extended period of time.

12 Claims, No Drawings

CYCLIC AMP DERIVATIVE-CONTAINING OINTMENT

This is a Continuation of application Ser. No. 08/009,110, filed Jan. 26, 1993, now abandoned.

FIELD OF THE INVENTION

This invention relates to an ointment containing an adenosine 3', 5'-cyclic phosphate derivative (hereinafter abbreviated as cAMP) and, more particularly, an ointment containing a cAMP derivative having improved stability.

BACKGROUND OF THE INVENTION

Drugs for treating various dermal ulcers include ointments, skin cleaning solutions, powders of water-absorbing high polymers, wound-covering patches and so on. These drugs contain, as active ingredients, an antibiotic, an antimicrobial, an enzyme, etc. In particular, ointments having water absorbing and drying properties are frequently applied to the affected skin area having exudate, such as dermal ulcers. The water absorbing and drying properties mean high hygroscopicity for absorbing and removing vulnerary water on the skin.

cAMP derivatives are known to be useful for treating various dermal ulcers as described, e.g., U.S. Pat. No. 4,873,227. The most effective bases with which the cAMP derivatives are applied to the treatment of various dermal ulcers are considered to be those having the above-mentioned water absorbing and drying properties.

However, since water-absorbing and drying bases contain water, when a hydrolyzable drug, such as a cAMP derivative, is combined therewith, the hydrolyzable drug has poor stability and the water-absorbing and drying base can hardly be used for an extended period of time. It has, therefore, been demanded to develop ointments comprising a cAMP derivative and a water-absorbing and drying base in which the cAMP derivative is stable.

It has been suggested to stabilize the cAMP derivative-containing ointments by incorporating sugars and/or inorganic high polymers therein as disclosed in U.S. Pat. No. 5,096,891. However, the stability achieved is still insufficient, needing further improvements.

SUMMARY OF THE INVENTION

Against this background, the inventors have conducted extensive investigations and, as a result, found that a powder of at least one salt whose aqueous solution has a pH of from 3 to 7 stabilizes the cAMP derivatives and provides ointments in which a cAMP derivative holds its efficacy for an extended period of time. The present invention has been completed based upon this finding.

The present invention provides a cAMP derivative-containing ointment comprising a water-absorbing and drying base having incorporated therein at least one salt whose aqueous solution has a pH of from 3 to 7.

DETAILED DESCRIPTION OF THE INVENTION

A cAMP derivative, e.g., sodium $N^6$,2'-O-dibutyryladenosine-3', 5'-cyclic phosphate, in an aqueous solution is most stable in the vicinity of pH 6. Generally, it is known that an active ingredient in ointments may be stabilized and prevented from hydrolyzing by adding a buffer agent. Included in this technique are interferon, tri- or higher valent sugar alcohol and an organic acid buffer agent having a buffering capacity at pH 3 to 6 (JP-A-59-196823 (the term "JP-A" as used herein means an "unexamined published Japanese patent application")), addition of a buffer solution to an O/W emulsion ointment of hydrocortisone butyrate to adjust to a pH of around 4 (Yasuaki Kawano, et al., *Yakuzaigaku*, Vol. 41, No. 2, pp. 71–81 (1981)), addition of a citric acid or sodium phosphate buffer solution to a Macrogol ointment of gabexate mesylate to adjust to a pH of 4 to 5 (Katsuro Shibata, et al., *Byoinyakugaku*, Vol. 15, No. 4, pp. 248–254 (1989), and addition of a citric acid solution to a lonapalene ointment to decrease the pH to 4 to 5 (Powell M. F., et al., *Int. Pharm.*, Vol. 44, No. 1/3, pp. 225–234 (1989)).

However, since decomposition of cAMP derivatives is chiefly due to hydrolysis, addition of an aqueous solution of a pH adjustor results in an increase in the water content which accelerates decomposition. Hence, if a salt whose aqueous solution has a pH of 3 to 7 or a mixture of such salts is added in the form of a powder, it would be dissolved in the base or a trace amount of water present in the base to provide a buffer which maintains the pH in a range in which the cAMP derivatives are stable. When the present invention is combined with other stabilizing means having different mechanisms, such as the above-mentioned addition of sugars, inorganic high polymers, desiccant or antioxidant, summation or synergism in the stabilizing effect is observed. That is, it is considered that the effect is enhanced by using, among the salts included in the scope of the present invention, a salt having both a pH adjusting function and another stabilizing function, such as a phosphate.

Examples of the cAMP derivatives which can be used as an active ingredient in the present invention include $N^6$-monoacyladenosine 3',5'-cyclic phosphate, 2'-O-monoacyladenosine 3',5'-cyclic phosphate, $N^6$,2'-O-diacyladenosine 3',5'-cyclic phosphate or those compounds substituted at the 8-position thereof with a mercapto group, a lower alkylthio group, a benzylthio group, an amino group, a hydroxyl group, a chlorine atom or a bromine atom; 8-benzylthioadenosine 3',5'-cyclic phosphate or its $N^6$-lower alkyl substituted compound; and 8-mercaptoadenosine 3',5'-cyclic phosphate. Preferred are sodium $N^6$,2'-O-dibutyryl-adenosine 3',5'-cyclic phosphate (hereinafter abbreviated as DBcAMP), sodium 2'-O-butyryladenosine 3',5'-cyclic phosphate, sodium $N^6$-butyryladenosine 3',5'-cyclic phosphate, sodium adenosine 3',5'-cyclic phosphate, 8-benzylthio-$N^6$-butyryladenosine 3',5'-cyclic phosphate and 8-benzylthioadenosine 3',5'-cyclic phosphate. These compounds may be used either singly or in combination of two or more thereof.

The water-absorbing and drying ointment bases (hereinafter simply referred to as an ointment base) which can be used in the present invention include polyethylene glycols having various molecular weights (preferably molecular weight of from 300 to 8000, more preferably combination of molecular weight of from 300 to 600 and molecular weight of from 3000 to 6000), polyhydric alcohols, e.g., glycerin, propylene glycol, and butylene glycol, or mixtures of these alcohols and higher alcohols, e.g., stearyl alcohol and cetyl alcohol. These ointment bases may be used either singly or as a mixture of two or more thereof at an arbitrary mixing ratio. In particular, polyethylene glycol (hereinafter abbreviated as PEG) or a combination of PEG's having different molecular weights, such as a mixture of PEG (400) and PEG (4000), are preferred.

The salts whose aqueous solutions have a pH of 3 to 7, which can be used for the stabilization of ointments (hereinafter simply referred to as stabilizing salts), include salts of inorganic acids, such as phosphoric acid, boric acid, and nitric acid, or organic acids, such as citric acid, carbonic acid, acetic acid, butyric acid, lactic acid, phthalic acid, maleic acid, succinic acid, tartaric acid, fumaric acid, gluconic acid, and oxalic acid, with an alkali metal, such as sodium, potassium, or lithium, an alkaline earth metal, such as calcium or magnesium, ammonium, or a nitrogen-containing organic base, such as glucamine or triethanolamine. These stabilizing salts are used either alone or in combination of two or more thereof so as to have a pH of from 3 to 7 when dissolved in water. Since oxidation of an ointment base is considered to adversely affect the stabilization of the cAMP derivative, it is preferable to use, among the above-mentioned stabilizing salts, those which inhibit oxidative decomposition of the ointment base, such as phosphates. Effective phosphates are sodium dihydrogenphosphate, potassium dihydrogenphosphate, disodium hydrogenphosphate and dipotassium hydrogenphosphate. These phosphates may effectively be used in combination. Morover, a particularly desirable embodiment is a sodium $N^6,2'$—O-di-butyryladenosine-3',5'-cyclic phosphate containing ointment comprising a base, wherein the base comprises polyethylene glycol (400), polyethylene glycol (4000), and either sodium dihydrogenphosphate or potassium dihydrogenphosphate.

The stabilizing salt(s) is/are dispersed in an ointment base either as such or, if necessary, after being ground to powder. While not limiting, the stabilizing salts are used in a total amount of from about 0.1 to about 20% by weight based on the base. For suppressing roughness to the touch so as to improve the feel on application and for making dispersion uniform, they are preferably used in a total amount of from 0.5 to 10% by weight, and more preferably 1% by weight.

The ointment of the present invention is prepared by known methods as described, for example, *Remington's Phamaceutical Sciences*, 18th edition, pp. 1602–1609 (1990) and *Prescription Phamacy*, pp. 216–226 (1963). For example, an ointment base is melted at about 60° to 70° C. To the resulting ointment base, a cAMP derivative and a stabilizing salt(s) are thoroughly mixed or kneaded to form a dispersion or a solution, followed by cooling to prepare an ointment. If desired, the ointment may further contain other stabilizing agents, such as dextrin, dextran, dried aluminum hydroxide gel, synthetic magnesium silicate, a desiccant (e.g., silica gel), and an antioxidant (e.g., threonine); and various additives common for ointments, such as various surface active agents, solubilizing agents, moisture retaining agents, antiseptics, colorants, and the like. The mixing or kneading of the components is carried out in a usual manner, for example, by means of a stirring machine (e.g., Three-One Motor manufactured by Heidon Co.), a Homo-mixer, etc.

Thus, the present invention provides a cAMP derivative-containing ointment which has improved stability over conventional ointments comprising a cAMP derivative dissolved or dispersed in a water-absorbing and drying base and, therefore, is useful for an extended period of time with a stable efficacy.

The present invention is now illustrated in greater detail with reference to the Examples, but it should be understood that the present invention is not deemed to be limited thereto. All the percents and ratios are by weight unless otherwise indicated.

COMPARATIVE EXAMPLE 1

| DBcAMP | 3.0% |
|---|---|
| PEG ointment base | 97.0% |
| (PEG 400/PEG 4000 = 70/30) | |

PEG 400 and PEG 4000 were put in a 1000 ml beaker at a ratio of 70:30 (g), melted at about 65° C. in a mantle heater, and cooled to prepare a PEG ointment base.

In a 200 ml beaker was put 97 g of the ointment base and re-melted at about 50° C. in a mantle heater. Three grams of DBcAMP were put in a warmed mortar, and the molten ointment base was added thereto in small portions and mixed therewith while warming. The mixture was allowed to cool with stirring to prepare 100 g of an ointment.

COMPARATIVE EXAMPLE 2

| DBcAMP | 3.51% |
|---|---|
| PEG 400 | 68.49% |
| PEG 4000 | 28.00% |

In a glass container were put 233.96 g of PEG 400 and 112 g of PEG 4000 and melted at 70° to 80° C. in a bench size quick homo-mixer "LR-2" manufactured by Mizuho Kogyo K.K., followed by cooling to about 50° C. A dispersion of 14.04 g of DBcAMP in 35 g of PEG 400, which had previously been prepared in a 100 ml beaker, was added to the PEG mixture. The beaker was washed with 15 g of PEG 400, and the washing was combined with the mixture. The mixture was mixed at about 50° C. for 10 minutes and then gradually cooled while continuously mixing to prepare 400 g of an ointment.

EXAMPLE 1

| DBcAMP | 3.00% |
|---|---|
| Phosphate mixture | 1.00% |
| PEG Ointment base | 96.00% |
| (PEG 400/PEG 4000 = 70/30 (g)) | |

Potassium dihydrogen phosphate and disodium hydrogenphosphate were separately ground in a small-sized grinding machine for analysis ("A-10" manufactured by IKA Co., Ltd.), sifted through a sieve of 150 mesh, and mixed together at such a ratio that the resulting mixed powder had a pH of 5 when dissolved in water (potassium dihydrogenphosphate/disodium hydrogenphosphate=97/3) to prepare a phosphate mixture.

In a 200 ml beaker was put 96 g of the same ointment base as used in Comparative Example 1 and melted at about 50° C. in a mantle heater. One gram of the phosphate mixture and 3 g of DBcAMP were thoroughly kneaded in a warmed mortar, and the molten ointment base was added thereto in small portions and kneaded while warming. The mixture was allowed to cool with stirring to prepare 100 g of an ointment.

EXAMPLE 2

| DBcAMP | 3.00% |
|---|---|
| Phosphate mixture | 1.00% |
| PEG Ointment base | 96.00% |
| (PEG 400/PEG 4000 = 70/30 (g)) | |

An ointment (100 g) was prepared in the same manner as in Example 1, except that the mixing ratio of the phosphates was changed so that the mixed powder showed pH 6 when dissolved in water (potassium dihydrogenphosphate/disodium hydrogenphosphate=82/18 (g)).

EXAMPLE 3

| DBcAMP | 3.00% |
|---|---|
| Phosphate mixture | 1.00% |
| PEG Ointment base | 96.00% |
| (PEG 400/PEG 4000 = 70:30 (g)) | |

An ointment (100 g) was prepared in the same manner as in Example 1, except that the mixing ratio of the phosphates was changed so that the mixed powder showed pH 7 when dissolved in water (potassium dihydrogenphosphate/disodium hydrogenphosphate=64/36 (g)).

EXAMPLE 4

| DBcAMP | 3.00% |
|---|---|
| Phosphate mixture | 3.00% |
| PEG Ointment base | 94.00% |
| (PEG 400/PEG 4000 = 70:30 (g)) | |

An ointment (100 g) was prepared in the same manner as in Example 1, except that 3 g of a 1:3 (g) phosphate mixture of sodium dihydrogenphosphate and disodium hydrogenphosphate which showed pH 7 when dissolved in water, was used.

EXAMPLE 5

| DBcAMP | 3.00% |
|---|---|
| Phosphate mixture | 1.00% |
| PEG Ointment base | 96.00% |
| (PEG 400/PEG 4000 = 70:30 (g)) | |

An ointment (100 g) was prepared in the same manner as in Example 1, except that the mixing ratio of the phosphates was changed so that the mixed powder showed pH 6 when dissolved in water (potassium dihydrogenphosphate/dipotassium hydrogenphosphate=79/21 (g)).

EXAMPLE 6

| DBcAMP | 3.00% |
|---|---|
| Phosphate mixture | 1.00% |
| PEG Ointment base | 96.00% |
| (PEG 400/PEG 4000 = 70:30 (g)) | |

An ointment (100 g) was prepared in the same manner as in Example 1, except that the mixing ratio of the phosphates was changed so that the mixed powder showed pH when dissolved in water (sodium dihydrogenphosphate/dipotassium hydrogenphosphate=96/4 (g)).

EXAMPLE 7

| DBcAMP | 3.00% |
|---|---|
| Sodium dihydrogenphosphate | 1.00% |
| PEG Ointment base | 96.00% |
| (PEG 400/PEG 4000 = 70:30 (g)) | |

An ointment (100 g) was prepared in the same manner as in Example 1, except for using 1 g of sodium dihydrogenphosphate.

EXAMPLE 8

| DBcAMP | 3.00% |
|---|---|
| Potassium dihydrogenphosphate | 1.00% |
| PEG Ointment base | 96.00% |
| (PEG 400/PEG 4000 = 70:30 (g)) | |

An ointment (100 g) was prepared in the same manner as in Example 1, except for using 1 g of potassium dihydrogenphosphate.

EXAMPLE 9

| DBcAMP | 3.00% |
|---|---|
| Dipotassium citrate | 3.00% |
| PEG Ointment base | 94.00% |
| (PEG 400/PEG 4000 = 70:30 (g)) | |

An ointment (100 g) was prepared in the same manner as in Example 1, except for using 3 g of dipotassium citrate.

EXAMPLE 10

In a glass container were put 219.96 g of PEG 400 and 112 g of PEG 4000 and melted at 70° to 80° C. in a bench size quick homo-mixer "LR-2" and cooled to about 50° C. A dispersion of 14.04 g of DBcAMP and 4 g of potassium dihydrogenphosphate having been ground and sifted in the same manner as in Example 1 in 35 g of PEG 400, which had previously been prepared in a 100 ml beaker, was added to the PEG mixture. The beaker was washed with 15 g of PEG 400, and the washing was combined with the mixture. The mixture was mixed at about 50° C. for 10 minutes and then gradually cooled while continuously mixing to prepare 400 g of an ointment.

EXAMPLE 11

In a glass container were put 215.96 g of PEG 400 and 112 g of PEG 4000 and melted and cooled in the same manner as in Example 10. To the PEG mixture was added a dispersion of 14.04 g of DBcAMP, 4 g of potassium dihydrogenphosphate and 4 g of aluminum hydroxide gel, the latter two having been ground and sifted in the same manner as in Example 1, in 35 g of PEG 400 (which had previously been prepared in a 100 ml beaker). The mixture was treated in the same manner as in Example 10 to prepare an ointment.

EXAMPLE 12

In a glass container were put 211.96 g of PEG 400 and 112 g of PEG 4000 and melted and cooled in the same manner as in Example 10. To the PEG mixture was added a dispersion of 14.04 g of DBcAMP, 4 g of silica gel (200 to 300 mesh; prepared by Kanto Kagaku K.K.), 4 g of potassium dihydrogenphosphate, and 4 g of aluminum hydroxide gel, the latter two having been ground and sifted in the same manner as in Example 1, in 35 g of PEG 400 (which had previously been prepared in a 100 ml beaker). The mixture was treated in the same manner as in Example 10 to prepare an ointment.

EXAMPLE 13

In a glass container were put 637.88 g of PEG 400 and 336 g of PEG 4000 and melted at 70° to 80° C. in T. K. Agihomo-mixer "HV-M" manufactured by Tokushu Kika Kogyo K. K. and cooled to about 50° C. A dispersion of 42.12 g of DBcAMP, 12 g of sodium dihydrogen phosphate, and 12 g of aluminum hydroxide gel, the latter two having been ground and sifted in the same manner as in Example 1, in 120 g of PEG 400 (which had previously been prepared in a 250 ml beaker) was added to the PEG mixture. The beaker was washed with 40 g of PEG 400, and the washing was combined with the mixture. The mixture was mixed at about 50° C. for 10 minutes and then gradually cooled while continuously mixing to prepare 1.2 kg of an ointment.

EXAMPLE 14

In a glass container were put 744.735 g of PEG 400 and 420 g of PEG 4000 and melted at 70° to 80° C. in T. K. Agihomo-mixer "HV-M" and cooled to about 50° C. A dispersion of 5.265 g of DBcAMP, 15 g of sodium dihydrogenphosphate, and 15 g of aluminum hydroxide gel, the latter two having been ground and sifted in the same manner as in Example 1, in 250 g of PEG 400 (which had previously been prepared in a 500 ml beaker) was added to the PEG mixture. The beaker was washed with 50 g of PEG 400, and the washing was combined with the mixture. The mixture was mixed at about 50° C. for 10 minutes and then gradually cooled while continuously mixing to prepare 1.5 kg of an ointment.

EXAMPLE 15

In a glass container were put 592.05 g of PEG 400 and 420 g of PEG 4000 and melted at 70° to 80° C. in T. K. Agihomo-mixer "HV-M" and cooled to about 50° C. A dispersion of 157.95 g of DBcAMP, 15 g of sodium dihydrogenphosphate, and 15 g of aluminum hydroxide gel, the latter two having been ground and sifted in the same manner as in Example 1, in 250 g of PEG 400 (which had previously been prepared in a 500 ml beaker) was added to the PEG mixture. The beaker was washed with 50 g of PEG 400, and the washing was combined with the mixture. The mixture was mixed at about 50° C. for 10 minutes and then gradually cooled while continuously mixing to prepare 1.5 kg of an ointment.

TEST EXAMPLE 1

Each of the ointments obtained in Comparative Example 1 and Examples 1 to 9 were filled in a glass bottle and preserved in a thermostat at 40° C. After 4 and 8 weeks, the DBcAMP content in the ointment was determined by high performance liquid chromatography in order to obtain a percent retention. The results obtained are shown in Table 1 below.

TABLE 1

| Formulation | DBcAMP Stability Percent Retention (%) | |
|---|---|---|
| | After 4 Weeks | After 8 Weeks |
| Comparative Example 1 | 71.18 | 57.97 |
| Example 1 | 91.82 | 79.40 |
| Example 2 | 90.85 | 83.67 |

TABLE 1-continued

| Formulation | DBcAMP Stability Percent Retention (%) | |
|---|---|---|
| | After 4 Weeks | After 8 Weeks |
| Example 3 | 85.93 | 75.28 |
| Example 4 | 89.11 | 83.56 |
| Example 5 | 92.81 | 78.50 |
| Example 6 | 91.41 | 86.31 |
| Example 7 | 93.93 | 89.13 |
| Example 8 | 92.96 | 88.81 |
| Example 9 | 81.50 | 71.20 |

The results in Table 1 demonstrate that the ointments of the present invention have a satisfactory stability when compared with the conventional ointment of Comparative Example 1.

TEST EXAMPLE 2

Each of the ointments obtained in Comparative Example 2 and Examples 10 to 13 were filled in a glass bottle and preserved in a thermostat at 40° C. After 4 and 8 weeks, the DBcAMP content in the ointment was determined by high performance liquid chromatography in order to obtain a percent retention. The results obtained are shown in Table 2 below.

TABLE 2

| Formulation | DBcAMP Stability Percent Retention (%) | |
|---|---|---|
| | After 4 Weeks | After 8 Weeks |
| Comparative Example 2 | 68.63 | 52.38 |
| Example 10 | 92.34 | 85.65 |
| Example 11 | 93.50 | 88.24 |
| Example 12 | 91.58 | 87.90 |
| Example 13 | 97.34 | 91.16 |

The results in Table 2 demonstrate that the ointments of the present invention have a satisfactory stability when compared with the conventional ointment of Comparative Example 2.

While the invention has been described in detail and with reference to specific examples thereof, it will be apparent to one skilled in the art that various changes and modifications can be made therein without departing from the spirit and scope thereof.

What is claimed is:

1. An ointment comprising an adenosine 3',5'-cyclic phosphate compound and a base having water-absorbing and drying properties; wherein, incorporated in said base, is one or more salts each having a pH in an aqueous solution of from 3 to 7; said one or more salts are present in a total amount of from 0.1 to 20% by weight of said base; said base having water-absorbing and dying properties is a polyethylene glycol, polyhydric alcohol, or mixtures thereof; and said one or more salts are added in the form of powder.

2. An ointment as claimed in claim 1, wherein said base having water-absorbing and drying properties is polyethylene glycol.

3. An ointment as claimed in claim 1, wherein said an adenosine 3',5'-cyclic phosphate compound is sodium $N^6,2'$-O-dibutyryladenosine 3',5'-cyclic phosphate.

4. An ointment as claimed in claim 1, wherein said one or more salts consists of at least one phosphate.

5. An ointment as claimed in claim 4, wherein said at least one phosphate consists of a mixture of potassium dihydrogenphosphate and disodium hydrogenphosphate.

6. An ointment as claimed in claim 4, wherein said at least one phosphate consists of a mixture of sodium dihydrogenphosphate and disodium hydrogenphosphate.

7. An ointment as claimed in claim 4, wherein said at least one phosphate consists of a mixture of potassium dihydrogenphosphate and dipotassium hydrogenphosphate.

8. An ointment as claimed in claim 4, wherein said at least one phosphate consists of a mixture of sodium dihydrogenphosphate and dipotassium hydrogenphosphate.

9. An ointment as claimed in claim 4, wherein said at least one phosphate consists of potassium dihydrogenphosphate.

10. An ointment as claimed in claim 4, wherein said at least one phosphate consists of sodium dihydrogenphosphate.

11. An ointment comprising sodium $N^6,2'$-O-dibutyryladenosine 3',5'-cyclic phosphate, a base, wherein said base comprises polyethylene glycol (400), polyethylene glycol (4000), and sodium dihydrogenphosphate.

12. An ointment comprising sodium $N^6,2'$-O-dibutyryladenosine 3',5'-cyclic phosphate, a base, wherein said base comprises polyethylene glycol (400), polyethylene glycol (4000), and potassium dihydrogenphosphate.

* * * * *